(12) United States Patent
Buerck et al.

(10) Patent No.: US 7,277,534 B1
(45) Date of Patent: Oct. 2, 2007

(54) COMMUNICATIONS SYSTEM AND METHOD

(75) Inventors: Axel Buerck, Taufkirchen (DE); Antonius Emmerink, Munich (DE); Egon Klein, Germering (DE); Harold Linke, Olching (DE); Helmut Rackl, Taufkirchen (DE); Johann-Heinrich Schinke, Munich (DE); Andreas Steffan, Munich (DE); Josef Wahler, Taufkirchen (DE); Rainer Windecker, Munich (DE); Steffi Winkler, Gauting (DE)

(73) Assignee: Siemens Aktiengesellschaft, Munich (DE)

( * ) Notice: Subject to any disclaimer, the term of this patent is extended or adjusted under 35 U.S.C. 154(b) by 181 days.

(21) Appl. No.: 10/069,792

(22) PCT Filed: Aug. 23, 2000

(86) PCT No.: PCT/DE00/02870

§ 371 (c)(1),
(2), (4) Date: Jun. 10, 2002

(87) PCT Pub. No.: WO01/17211

PCT Pub. Date: Mar. 8, 2001

(30) Foreign Application Priority Data

Aug. 31, 1999  (DE) .............................. 199 41 345

(51) Int. Cl.
*H04M 7/00* (2006.01)

(52) U.S. Cl. ............................ 379/220.01; 379/221.01; 370/395.2; 370/395.21; 370/352

(58) Field of Classification Search ................ 379/219, 379/220.01, 221.01; 370/395.2, 395.21, 370/352
See application file for complete search history.

(56) References Cited

U.S. PATENT DOCUMENTS 6,487,170 B1 * 11/2002 Chen et al. ................. 370/231

FOREIGN PATENT DOCUMENTS

| DE | 3606846 A1 | 10/1987 |
| DE | 40 18 383 C2 | 12/1991 |
| EP | 0 920 234 A2 | 6/1999 |
| WO | WO93/15583 | 8/1993 |

* cited by examiner

*Primary Examiner*—Quynh H. Nguyen
(74) *Attorney, Agent, or Firm*—Morrison & Foerster LLP

(57) ABSTRACT

A method and an arrangement are specified for setting up and clearing communications links via a private branch exchange. The transport network for transporting the communication data is preferably in the form of an ATM network or IP network, and is controlled by a separate control network, separated from it. The advantage is that the two networks are independent of one another, and that broadband communications requirements can be satisfied easily by a modular expansion capability. The central control configuration allows already existing central databases relating to subscribers to be used, and likewise allows connection-related service feature control systems still to be used.

19 Claims, 4 Drawing Sheets

COMMUNICATIONS SYSTEM AND METHOD

CLAIM FOR PRIORITY

This application claims priority to International Application No. PCT/DE00/02870 which was published in the German Language on Mar. 8, 2001.

TECHNICAL FIELD OF INVENTION

The invention relates to a method and system for setting up and clearing communications links, and in particular, to a private branch exchange and terminals connected thereto.

BACKGROUND OF THE INVENTION

The increase in the amount of traffic resulting from the rising number of communications subscribers, as well as more stringent requirements for the amount of data to be transmitted, means that switching devices, such as private branch exchanges, are subject to ever more stringent requirements. For example, the amount of data to be transmitted per communications link, and the number of communications terminals which can be connected to one another. Present-day devices are based, for example, on the TDM method (Time Division Multiplexing) in which communication data relating to different connections is transmitted in respectively defined time slots. Connection between different communications partners is produced by a switching matrix, which allocates incoming time slots on an incoming connection to outgoing time slots on an outgoing connection, on the basis of control information. Switching matrices such as these are generally of a fixed size and can produce only a defined number of connections, which often makes it harder to adapt switching systems to meet the requirements. Devices such as these have a further problem in that the time slots can hold a limited amount of data. For example, a switching matrix can produce 4096 connections, while a maximum of 64 KBits of data can be transmitted within one time slot. An increasing number of subscribers can thus only ever be coped with in groups of 4096 connections. However, utilization of these different extension levels demands additional development effort to match the switching device to the greater number of subscribers. It is likewise impossible without problems to increase the amount of communication on each connection in a flexible manner, and this can best be done by setting up two or more communications links, e.g. in the form of a 64 kbit fit. In practice, this type of bandwidth duplication has, however, not been implemented for ISDN (Integrated Services Digital Network) transmission, and scarcely any terminals are available for this purpose.

SUMMARY OF THE INVENTION

In one embodiment of the invention, there is a method and system for providing a communications link, which allow a high level of flexibility with regard to matching to the number of communications links to be provided, matching to the amount of communication per connection, and to their physical extent.

In one aspect, control and connection functions are carried out in an advantageous manner by functional units which are physically separated from one another, since this allows distributed switching systems with the advantageous characteristics of central systems to be set up without any major development effort.

According to the invention, the control function is advantageously provided in a control network, and the connection function is offered via a transport network, advantageously with the assistance of a connection device which may reside on a transport network of any desired type that is available and is suitable depending on the type of application.

Hence, an increased amount of communication can be dealt with by an appropriately designed transport network with an adequate transmission capacity, while the control, for example of a control network, need not be expanded, and can remain in its already existing form. Furthermore, the method ensures that decentralized communications arrangements which are distributed over a physically large area can be operated in which, the control information to a central control device is handled, while the communications links are provided via a separate transport network of suitable topology.

According to another aspect of the invention, when using a central control device, existing databases and control methods for a central switching device can still advantageously be used in order to control decentralized switching devices in the transport network in order to provide a communications link. This ensures smooth migration of existing solutions to the described new solution, while retaining the advantages of central data administration, as well as defect identification and rectification, with greater flexibility.

In another aspect, connections are set up via decentralized devices in the transport network. This advantageously allows transport connections to be provided within a decentralized device, whose data streams therefore do not place any load on the central controller. A high level of redundancy is achieved and switching devices can in each case be used for the transport network, for example at the moment, ATM, Ethernet or IP switching devices.

In another embodiment of the invention, one central device controls the decentralized switching devices in a particularly advantageous manner. This allows a number of decentralized devices to be connected to one another which, together, behave like a single switching device. In this way, connection-related service features, which are implemented centrally, can be provided for communications links via the transport network without needing any additional development work with regard to the transport network. There is likewise no need for adaptations to the existing service features at the control end in order to make them available throughout the network. It is also advantageous to use methods such as this in distributed switching devices throughout the network, which would otherwise be available in a single local switching device, and not in a number of switching devices. Applications and interfaces for applications which until now have been able to access only single systems can thus advantageously be used for the decentralized switching devices as well.

In still another embodiment, terminals which can be accessed by a time slot multiplexing connection can advantageously be connected via the transport network, with new suitable connection information being generated in the controller from conventional time-slot-related connection information, in order to control the provision of a communications link via the transport network. This allows already existing methods to be used to control TDM switching matrices, in order to set up connections based on this variant of the method.

However, the method is also suitable, without any restrictions, for other dynamically set-up connections, such as ATM connections or IP connections. For the controller, these connections appear to be similar to conventional TDM connections, and are also processed in the same way, specifically with conventional time-slot-related connection information also being generated for this purpose, which is then in turn converted to new connection information, matched to the transport network. This also allows terminals which are not time-slot-related (not TDM-based) to be connected, such as IP or ATM terminals, e.g. IP telephones, computers and ATM terminals.

Already existing methods for controlling TDM connections can be used in this way in order to set up other connections.

This advantageously reduces the technical implementation effort and makes it easier for existing methods to migrate to new methods, since all that is necessary is for the control information to be matched to the requirements of the transport network.

In yet another embodiment, transport network connections are produced in a particularly advantageous manner by using an asynchronous transfer mode, since ATM networks are technically proven and offer a basis for greater transport capacities and more flexible distribution of them. Furthermore ATM networks are particularly suitable for the time-critical transmission of high data rates via decentralized switching devices, since they can guarantee the quality features (quality of service) required for voice and moving pictures.

In still another embodiment, service features are provided in a particularly advantageous manner via the central control device, since this allows any desired transport network to be supplied to an existing service feature control network. Furthermore, this advantageously allows already existing methods to be used to provide service features, and there is no need for independent service feature control adaptation for each transport network. In this way, the transport network can be replaced without any major control reactions.

In another embodiment of the invention, there is a system including, for example, a communications link which has a separate control network, in particular for transmitting signaling information, and a separate transport network, in which the transport network is controlled by the control network via suitable means. The separation of the control network and transport network relates to the information routes through the network, e.g. to the logical topology of the networks. Physically, it is possible to use different networks or the same network for transmission. In this way, a minimal configuration is specified to solve the problem of specifying a communications arrangement which can be expanded in a flexible manner for any desired data transmission rates. They can also advantageously be adapted on a subscriber-specific basis.

In one aspect, the transport network Advantageously has a decentralized device for connection of a communications terminal, and a decentralized switching device, which is provided in the area of the decentralized device, in order to provide a communications device in the transport network. This makes it possible to supply large areas with communications links via a single private branch exchange, with the capability to keep the wiring complexity at a minimal level, since the control network is routed to a control center, while the most suitable topology, even in the context of already laid or public networks, can be chosen for connecting the decentralized switching devices through the transport network.

In one aspect of the system, there is a central control device in the control network, since this makes it possible for the subscriber administration and connection control, as well as the data storage, maintenance and protection associated with them, problem identification and rectification, and supply of new software issue standards to be carried out centrally.

In another aspect of the system, the central control device is advantageously operatively connected to a device for providing service features. This may also be an integral component of the control device since this allows central provision of connection-related service features and other service features with minimal installation and implementation effort. In addition to service features, the device for providing service features can also provide further applications and/or an interface to applications which go beyond communications service features. External servers, for example for call center solutions, CTI (Computer Telephony Integration) can thus advantageously be connected in a centralized manner via standardized interfaces.

According to one aspect, a private branch exchange can advantageously be set up, which combines at least two decentralized switching devices with a central control device since this provides a distributed private branch exchange in the form of a minimal configuration, which can be expanded in a modular manner as required.

In another aspect of the configuration, there is a device for providing connection-related service features and other service features, since this means that there is no need for the respective decentralized provision and implementation of the service features in the transport network for this private branch exchange.

It is advantageous to have an emergency control device in the region of at least one decentralized device, which allows emergency operation between communications terminals which are connected to this decentralized device, if the central control device fails or the control network is interrupted. This achieves a very high level of availability with a single system, corresponding to the availability of networked systems.

BRIEF DESCRIPTION OF THE DRAWINGS

Exemplary embodiments of the invention will be explained in more detail in the following text with reference to figures.

DETAILED DESCRIPTION OF THE PREFERRED EMBODIMENT

Figure 1:
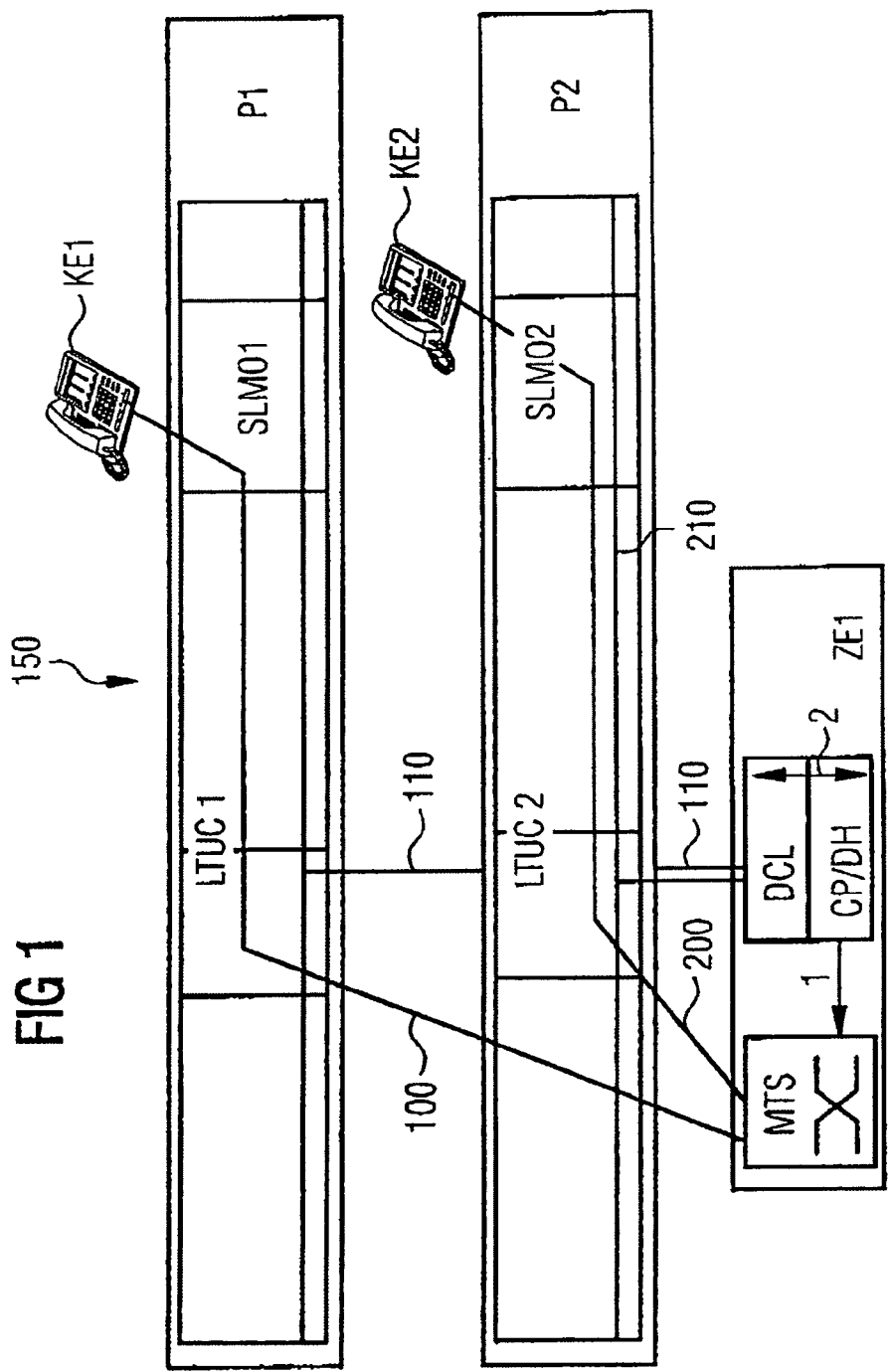
FIG. 1 shows a conventional communications arrangement.

FIG. 1 shows an example of a known private branch exchange 150 having two peripheral devices P1 and P2 to which a respective communications terminal KE1 or KE2 is connected, operating on a digital or analog basis. These peripheral devices P1 and P2 are accommodated in the same physical area as the central device ZE1. For example, they are located in the same room or in the same cabinet with it. The terminals fill defined time slots in PCM data streams (Pulse Code Modulation) with communication data. The digital or analog communications terminals KE1 and KE2 are connected to respective subscriber line modules SLMO1 and SLMO2 which add to or take from the PCM data stream digital data which is intended for the respective terminals or originates from the respective terminals, via time slots which are defined by signaling. These PCM data streams are designated 100 and 200, respectively, in FIG. 1. Furthermore, signaling connections are shown, which are represented by 110 and 210, respectively. It should be noted that this is only a logical representation, and is not a physical representation. However, in reality, the transport data and the signaling data are transmitted in the same connecting cable.

Furthermore, peripheral devices P1 and P2 as well as line trunk units LTUC1 and LTUC2 are shown here, which control the data traffic to the subscriber line modules of respective decentralized devices. The peripheral device P1 is supplied with signaling data via the line 110 and the peripheral device P2 is supplied with signaling data via the signaling line 210.

As illustrated, both the information to be transported and the signaling information are supplied to a central device ZE1 in this arrangement. In this case, messages 2 are collected and distributed by a message device DCL, and are interchanged between the central device ZE1 and peripheral devices P1, P2. The call processing CP controls the setting up and clearing of connections and uses, for example, equipment-specific interface functions DH which, for example, are in the form of program modules. Setting commands 1 for the switching matrix MTS are produced in this way. These setting commands essentially indicate which input of the switching matrix should be connected to which output in order to produce a communications link. The control function and connection function are thus carried out by a single physically integrated functional unit in the communications network.

Problems occur with configurations such as these, since the data to be transported should be supplied to the central device ZE1. This is true even when, for example, two communications terminals which are connected to the same peripheral device P1 wish to communicate with one another. The wiring complexity that needs to be accepted in such devices increases with the distance between the terminals and the central device ZE1, so that this type of arrangement restricts extension of the area covered by a private branch exchange, or makes the installation considerably more expensive when covering relatively large areas.

One alternative to extension of the area covered by an individual device 150 would be to network a number of devices 150, although this would result in the advantages of a single system being lost. When networking a number of such devices 150, one exacerbating factor is that additional trunk assemblies with additional connecting cables must be provided and installed in each case.

Problems likewise occur in such devices with the modular expansion capability, not only in the number of connections but also in the amount of data which can be transmitted. By way of example, the switching matrix MTS may be provided as one entity. This means that, in the extreme, a new switching matrix with, for example, 4096 connections must be purchased and installed for one additional connection. The transmission rate in such systems is limited, for example, by the capability to transmit a maximum of 64 KBits or some other administratively defined or technically restricted amount of data, in each time slot, as is specified by the ISDN Standard. This type of configuration also makes it impossible to use different data rates on each individual communications link.

Figure 2:
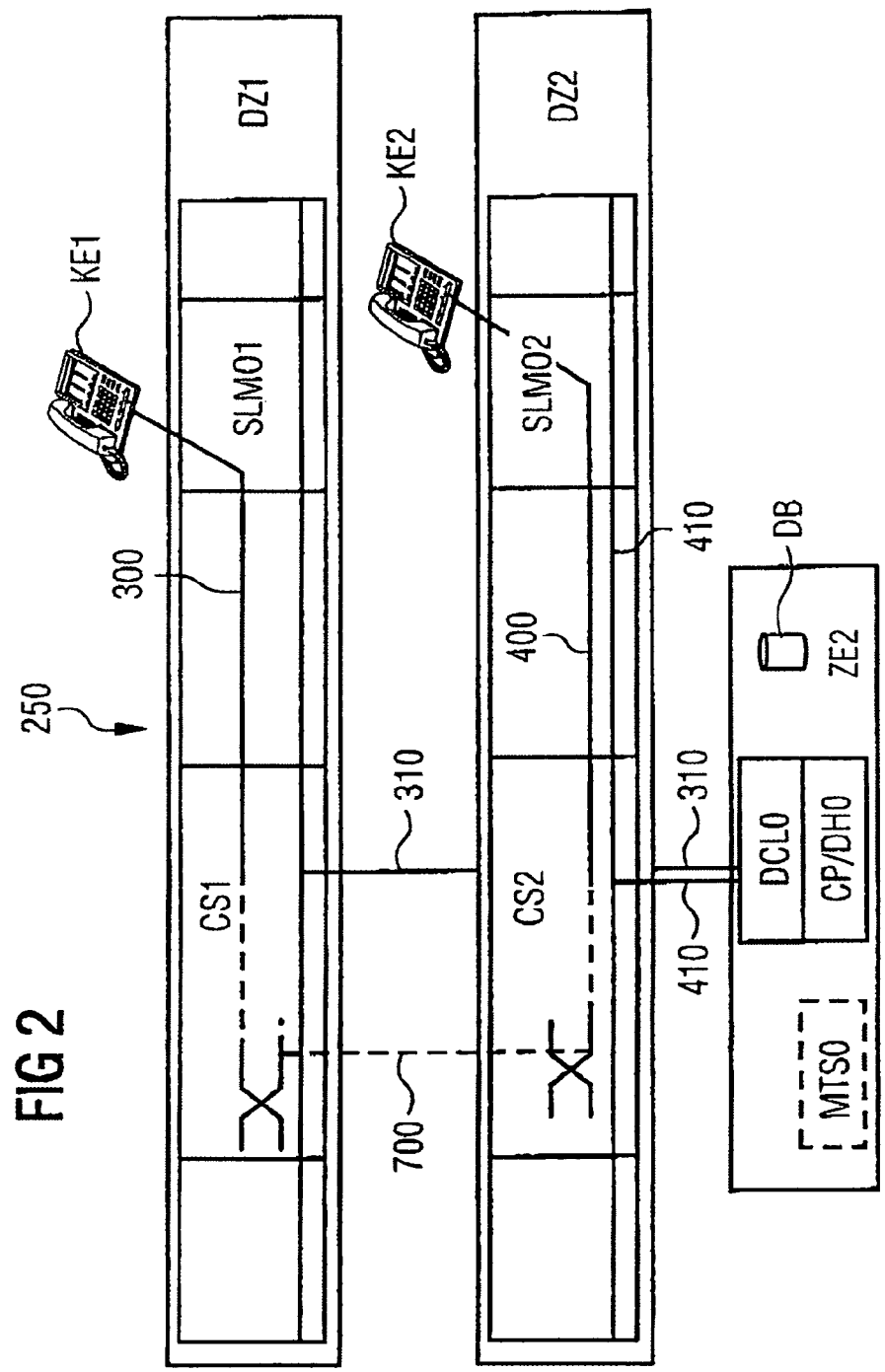
FIG. 2 shows an example of a communications arrangement in the invention.

FIG. 2 shows an example of a new arrangement for setting up communications links. By way of example, this arrangement shows the layout of a private branch exchange 250.

Components of the device which are the same as those in FIG. 1 have the same reference symbols in FIG. 2. Referring now to FIG. 2, it is immediately evident that there is a separate transport network 700 and a separate control network 310/410 in this case. This layout of a switching system has the advantage that already existing networks, such as public or private networks, can be used for the transport network. In this case, the control network just needs to be routed to the central device ZE2.

The digital or analog communications terminals KE1 and KE2 are illustrated here as being connected to respective subscriber line modules SLMO1 and SLMO2. However, without any restrictions to the invention, it is also feasible to integrate terminals in an arrangement 250 such as this which can be connected directly to the transport network 700, bypassing, or without, SLMO. It is thus also possible to connect ATM terminals or else IP-based (Internet Protocol) terminals.

As illustrated, the decentralized devices DZ1 and DZ2 have respective decentralized switching devices CS1 and CS2 which may, for example, be in the form of ATM access devices. The illustration likewise shows that the switching matrix MTS0 is no longer used for connection tasks. Rather, the transport network carries out the connection tasks.

In this arrangement, at least one control information item is in each case provided for setting up the communications link for the respective decentralized switching devices CS1 and CS2 via the control lines 410 and 310 for this purpose, with this control information item being derived from time-slot-related control information. Furthermore, the figure shows that PCM data is converted on a respective data path 300 or 400 to cell data in accordance with the Standard of the transport network 700, such as ATM cell data. In this case, it should be noted that the use of an ATM network as the transport network serves as an exemplary embodiment in this case. Ethernets, other IP connections or even TDM connections can likewise be used for this purpose. The choice is dependent on the intended application and covers the entire range of available networks, both in the narrowband field and in the broadband field.

Since there are no communications links to the central device ZE2 in FIG. 2, there is also no need in this embodiment to incur call charges for any connections of DZ1 and DZ2 to the central device ZE2 via public lines, for example tie lines, as would have been the case for communication from DZ1 to DZ2 until now with a remote peripheral device 150 from FIG. 1. Call processing which is independent of the transport network but which is restricted essentially to basic call functionality is preferably carried out in the decentralized switching devices CS1 and CS2. Service features are provided by the central controller ZE2. Connections between the various decentralized devices are controlled by the central device ZE2 via signaling. The advantages of this arrangement are that it has both a narrowband and broadband capability. Furthermore, the transport network can be set up for both public networks and private networks, or else for a combination of both. In addition, it is possible to allocate to the central device ZE2 decentralized devices at a physically unrestricted distance away, so that even very large devices can be provided by such a private branch exchange, which are in turn used to supply communications links for large areas. By retaining a central control device, it is possible to continue to use already existing software with minimal changes. If one were to distribute the control process, or else the switching matrix, then new methods would need to be developed for control and a mechanism would have to be provided to ensure consistency between distributed databases. A further advantage of such a device 250 over a networked system composed of devices 150 is that the distributed system is a single system, for which reason it is likewise possible to provide service features which are implemented within the system. There is thus no need to convert individual service features to provide them with the capability for operation on a network.

Figure 3:
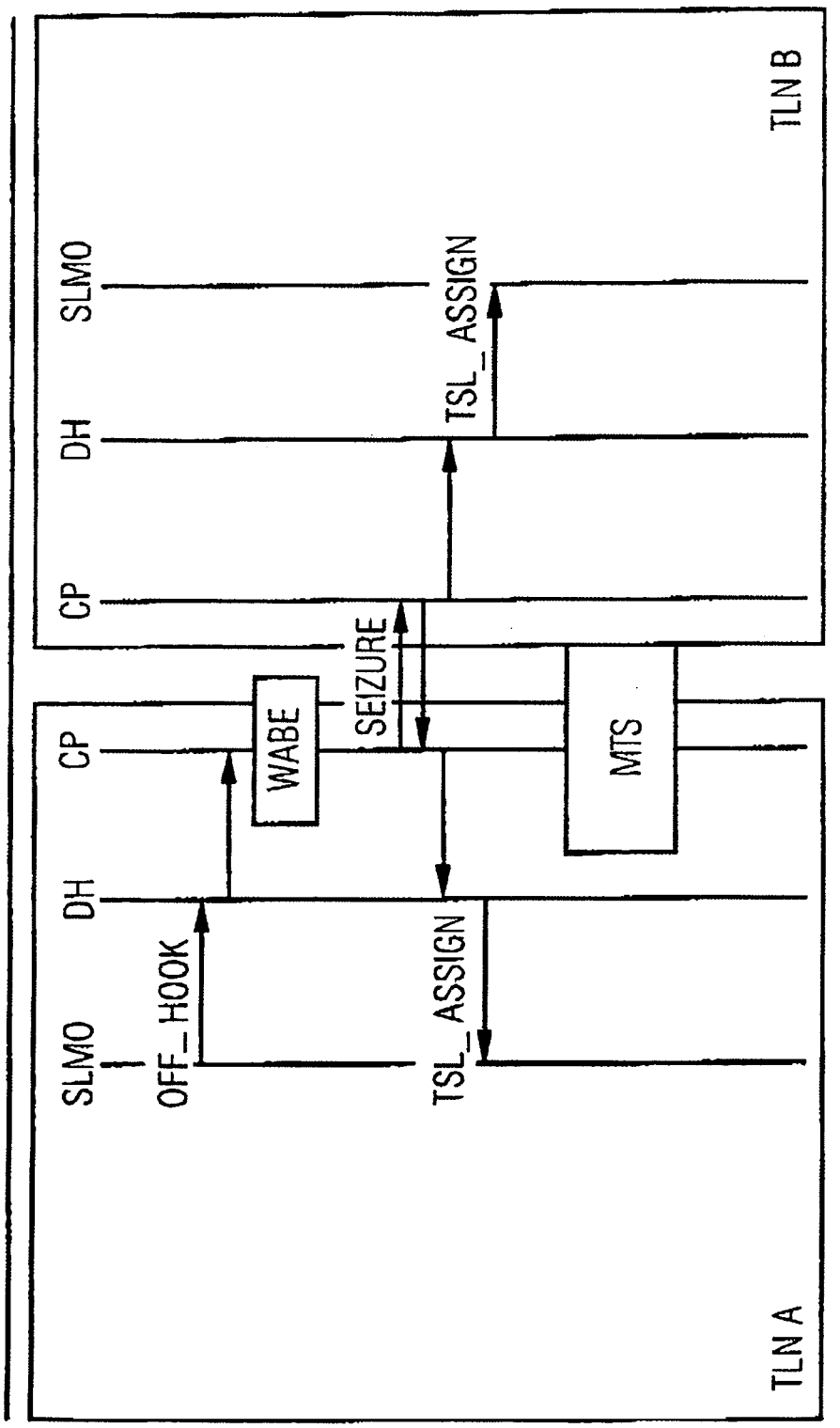
FIG. 3 shows an example of a message sequence in a known switching system.

By way of example, FIG. 3 shows a message sequence in a conventional communication system for setting up a connection between two peripheral devices to which the terminal of a subscriber A, TLNA and the terminal of a subscriber B, TLNB are connected. The time sequence of the messages, and control messages, is from top to bottom. First, the subscriber A goes off hook and generates the signaling information OFF HOOK. The desired communication partner is then dialed by entering dialing information, which is passed on from an equipment-specific interface module DH to the call processing CP for the subscriber A.

The dialing assessment WABE of the dialing information leads to a message SEIZURE being passed to the call processing CP for the subscriber B. An equipment-specific interface module DH, which has the responsibility there, assigns to the connection an explicit time slot, for example, ZS1 on a defined PCM data path, for example PD1, and generates the control message TSL_ASSIGN to the subscriber line module SLMO1. This control message tells the subscriber line module SLMO1 the explicit time slot ZS1 and the defined PCM data path PD1 which is intended to be used for that connection. The explicit time slot ZS1 in the PCM data path PD1 applies to the connection element between the subscriber line module SLMO1 and the MTS. A second explicit time slot ZS2 in a second explicitly defined PCM data path PD2 applies to the connection element between the MTS and the subscriber line module SLMO2. The information ZS2 and PD2 is in turn signaled to the subscriber line module SLMO2 in a control message TSL_ASSIGN. Generally, TDM based private branch exchanges use a TDM switching matrix MTS for physical connection of individual subscribers. A setting command PATH_CONNECT1 is produced for this switching matrix and results in the time slot ZS1 being connected from the PCM data path PD1 to the time slot ZS2 for the PCM data path PD2. The two connection elements are thus connected to form a continuous path between SLMO1 and SLMO2.

In this case, in conjunction with the embodiment of the method, it is irrelevant whether the CP and DH are components of the control software, or whether they are in the form of individual modules or are integrated.

Figure 4:
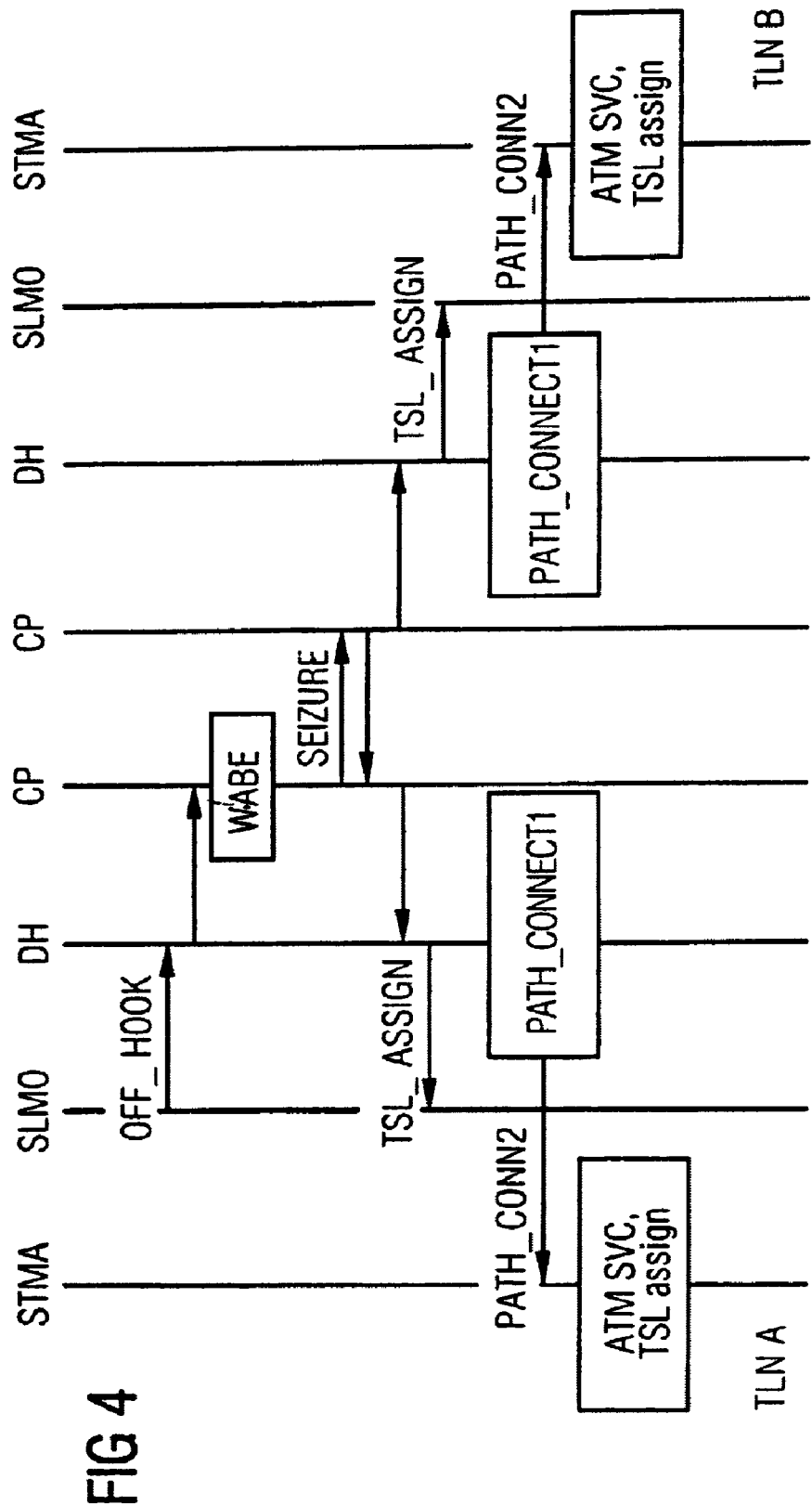
FIG. 4 shows an example of a message sequence using time-slot-related connection information for the transport network.

By way of example, FIG. 4 shows a message sequence between two decentralized devices, to which the terminal of a subscriber A, TLNA and the terminal of a subscriber B, TLNB are connected. In this case, an ATM network is used, by way of example, as the transport network. The time sequence of the messages or signaling messages, is from top to bottom. A functional unit STMA converts the time slot for the PCM data stream to a cell stream of ATM cells. In FIG. 2 a device such as this is integrated in each of the decentralized switching devices CS1 and CS2, and for this reason is not shown separately.

The sequence differs from the sequence illustrated in FIG. 3 from the point where the setting command PATH_CONNECT1 is produced for the TDM switching matrix. Instead of a setting command PATH_CONNECT1, a control message PATH_CONN2 is generated, which is sent to the decentralized switching devices. The decentralized switching devices then set up a connection on the transport network. When using an ATM transport network, by way of example, an ATMSVC is set up (ATM Switched Virtual Connection) by means of ATM signaling methods.

The control message PATH_CONN2 includes the time slot and data path information ZS and PD, which can be obtained, for example, directly from the setting message PATH_CONNECT1. Furthermore, the central control device specifies the transport-network-dependent address of that decentralized switching device for which the connection is intended to be set up. This means that the data which is provided as information via the transport network for the central control is restricted to the transport-network-dependent addresses of the respective decentralized switching devices. The central control device once again determines the necessary addresses from the time slot and data path information ZS and PD. Allocation tables in a central database DB control the mapping of the time slot/data path to the decentralized switching device.

The control message PATH_CONN2 may also include other information, and the control message PATH_CONNECT may also be generated in a number of more specific forms. If it is intended to set up connections with different bandwidths, the control message PATH_CONN2 may also include information about the desired bandwidth. Alternatively, the bandwidth information can also be interchanged directly between the subscriber line module and the switching device.

When the decentralized switching devices have set up a connection in the transport network 700 after receiving the message, PATH_CONN2, the user data is then transmitted via this transport network 700. The allocation of a user data stream on the data path 300/400 between the subscriber line module and the decentralized device DZ to a connection between DZ1 and DZ2 is produced by mapping time slot details ZS and PD to form a connection identifier for the connection. This means that, despite the possibly complicated sequences for setting up a connection via the transport network from the central controller ZE2, preferably only these addresses need to be passed on to the call processing for the transport network in order to set up a connection via this transport network. The transport-network-specific call processing handles the rest.

According to this message sequence, the PATH CONNECT command is thus replaced by transport-network-specific call processing. In order to allow TDM-based subscribers to be connected by decentralized switching devices independently of the transport network, it is necessary to convert time slots to transport units. This is done in a conversion unit, such as STMA, of which each decentralized device has at least one, which is preferably looped into the path of the user data. An ATM-PCM gateway or an IP-PCM gateway can be provided for this purpose.

The TDM-based subscriber line modules communicate with the conversion unit via, for example, connections on a backplane motherboard in the respective decentralized device. A bus which connects the assemblies to one another can be provided for this purpose on the printed circuit board. The setting commands for looping in the conversion unit are for this purpose preferably produced autonomously from the PATH_CONN2 message by the decentralized switching device.

However, the method is not restricted to dial connections that are set up dynamically, but can likewise control an ATMPVC (ATMPVC Permanent virtual connection). The information related to the address must then be interchanged with information controlling the use of fixed connections. Other forms of data transmission may also still be used, such as IP connections.

The invention claimed is:

1. A method for setting up and/or clearing a communications link, comprising:
   setting up and/or clearing a communications link for transporting communication data which is carried out by at least one first functional unit in a communications network, the at least one first functional unit carrying out basic call functionality which is independent of a transport network; and
   controlling a connection function which is carried out by a second functional unit in the communications network, the second functional unit providing supplementary features to enhance a narrowband network functionality, and controlling connections between the at least one first functional units via signaling,
   wherein the first and the second functional units are physically separated from one another, and
   connection related service features are provided via the transport network.

2. The method as claimed in claim 1, further comprising:
   signaling to control the setting up and/or clearing of a communications link,
   wherein the connection is set up and/or cleared via a transport network; and
   signaling is carried out via a control network.

3. The method as claimed in claim 2, in which the signaling is controlled by a central device.

4. The method as claimed in claim 1, further comprising setting up the communications link in the transport network via at least one decentralized device.

5. The method as claimed in claim 3, wherein the central device controls a decentralized switching device.

6. The method as claimed in claim 1, further comprising setting up and/or clearing a communications link to a communications terminal, and setting up the connection via the transport network by producing at least one time slot control information item in the central device, which information item is used for setting up connections in the transport network.

7. The method as claimed in claim 6, linking the time slot control information is to transport-network-specific information and transmitting to a decentralized device.

8. The method as claimed in claim 1, wherein an asynchronous transmission method is used for transmission via the communications link.

9. The method as claimed in claim 2, further comprising providing at least one connection-related service feature and/or a service feature or application, related to the central device by the central device.

10. An arrangement for setting up and/or clearing a communications link, comprising:
    a transport network to provide a communications link;
    a control network to control the setting up and/or clearing of the communications link;
    at least one unit to carry out basic call operations; and
    a device to control the setting-up and/or clearing of connections in the transport network by a control network, to provide supplementary features to enhance a narrowband network functionality, and to control connections between the at least one unit via signaling,
    wherein the device is arranged such that it is physically separated from the transport network and the at least one unit, and
    connection related service features are provided via the transport network.

11. The arrangement as claimed in claim 10, in which the transport network has at least one decentralized device to connect with a communications terminal, and has a switching device in the region of the decentralized device to provide a communications link in the transport network.

12. The arrangement as claimed in claim 10, in which the control network has a central device for control.

13. The arrangement as claimed in claim 11, which has a central device to provide at least one connection-related service feature and/or a service feature or application relating to a central device, the device being operatively connected to the central device.

14. The arrangement as claimed in claim 10, which is in the form of a private branch exchange and has at least two decentralized devices for connection of communications terminals.

15. The arrangement as claimed in claim 10, wherein in the region of the decentralized device, there is a control device to provide a communications link in the region of this decentralized device, if the central control device is not available.

16. The method as claimed in claim 4, in which the central device controls a decentralized switching device.

17. The arrangement as claimed in claim 11, which is in the form of a private branch exchange and has at least two decentralized devices for connection of communications terminals.

18. An arrangement for setting up and/or clearing a communications link, comprising:
    a transport network to provide a communications link;
    a control network to control the setting up and/or clearing of the communications link; and
    a device to control the setting-up and/or clearing of connections in the transport network by a control network, to provide supplementary features to enhance a narrowband network functionality,
    wherein the device is arranged such that it is physically separated from the transport network, and
    connection related service features are provided via the transport network.

19. An arrangement for setting up and/or clearing a communications link, comprising:
    a transport network to provide a communications link;
    a control network to control the setting up and/or clearing of the communications link;
    a device to control the setting-up and/or clearing of connections in the transport network by a control network,
        wherein the device is arranged such that it is physically separated from the transport network,
        the transport network has at least one decentralized device to connect with a communications terminal, and has at least one switching device in the region of the at least one decentralized device to provide a communications link in the transport network and to provide basic call operations,
        connection related service features are provided via the transport network, and
        the control network has a central device for control; and
    a device to provide at least one connection-related service feature and/or a service feature or application relating to a central device, to provide supplementary features to enhance a narrowband network functionality, and to control connections between the at least one switching devices via signaling, the device being operatively connected to the central device.

* * * * *